(12) United States Patent
Ho

(10) Patent No.: US 7,544,822 B2
(45) Date of Patent: Jun. 9, 2009

(54) RECOVERY OF PHYTONUTRIENTS FROM OILS

(75) Inventor: David Sue San Ho, Ipoh (MY)

(73) Assignee: Carotech Bhd., Chemor, Perak (MY)

( * ) Notice: Subject to any disclaimer, the term of this patent is extended or adjusted under 35 U.S.C. 154(b) by 90 days.

(21) Appl. No.: 10/579,637

(22) PCT Filed: Nov. 18, 2004

(86) PCT No.: PCT/US2004/038774

§ 371 (c)(1),
(2), (4) Date: May 9, 2007

(87) PCT Pub. No.: WO2005/051294

PCT Pub. Date: Jun. 9, 2005

(65) Prior Publication Data

US 2007/0238886 A1    Oct. 11, 2007

(30) Foreign Application Priority Data

Nov. 19, 2003    (MY) .............................. PI 20034440

(51) Int. Cl.
*C07C 51/23*    (2006.01)
(52) U.S. Cl. ...................... 554/175; 554/208; 552/502; 552/545; 549/413
(58) Field of Classification Search .................. None
See application file for complete search history.

(56) References Cited

U.S. PATENT DOCUMENTS 5,660,691 A    8/1997    Barnicki et al.

*Primary Examiner*—Deborah D Carr
(74) *Attorney, Agent, or Firm*—David G. Oberdick, Esq.; Meyer, Unkovic & Scott LLP

(57) ABSTRACT

The present invention relates to an improved and integrated process for the extraction and purification of tocotrienols or tocopherols, carotenoids and sterols from vegetable and other edible oils. Fatty acids in the vegetable oils are subjected to alcoholic osterification to form ester-rich layer that includes fatty acid alkyl esters, carotenoids, tocotrienols or tocopherols, and sterols. The advantages of this process are that the tocotrienols or tocopherols, carotenoids and sterols are produced efficiently without any substantial decomposition or degradation of these phytonutrients.

67 Claims, No Drawings

RECOVERY OF PHYTONUTRIENTS FROM OILS

This application is filed under 35 U.S.C. § 371 and hereby claims priority to its Patent Cooperation Treaty filing date of Nov. 18, 2004, and to its Patent Cooperation Treaty priority date of Nov. 19, 2003.

TECHNICAL FIELD OF THE INVENTION

The present invention generally relates to the recovery of phytonutrients from oils and more particularly to an integrated process for the extraction and purification of tocotrienols or tocopherols, carotenoids and sterols from vegetable and other edible oils.

BACKGROUND OF THE INVENTION

Vitamin E is one of the most popular and most often used vitamin in the US. The term vitamin E is now considered to be the generic name describing both the tocopherols and tocotrienols. Structurally, tocopherols and tocotrienols share some resemblance. However, tocopherols and tocotrienols are distinguished by their side chains. While tocopherol has a saturated tail, tocotrienol possesses an unsaturated isoprenoid side chain. Tocopherols and tocotrienols are further separated into individual compounds assigned by the Greek letter prefixes—alpha, beta, gamma and delta ($\alpha, \beta, \delta, \gamma$). Tocotrienols and Tocopherols are found in the normal diet such as cereal grains such as wheat barley and rye. They are also found in high level in vegetable oils such as safflower, soybean, peanut, cottonseed, linseed, sunflower, rapeseed, palm and other vegetable sources. Crude palm oil and rice bran oil contain high levels of both tocotrienols and tocopherols.

Tocotrienols are known for their hypocholesterolemic effects and have been shown to decrease the blood level of the low-density lipoprotein cholesterol and the total serum cholesterol, while increasing the ratio of the high-density lipoprotein cholesterol to the low-density lipoprotein fraction (Qureshi et al., *American Journal of Clinical Nutrition*, 1991: 53: 1042S-1046S; Bierenbaum M L, et al., *Asia Pacific Journal of Clinical Nutrition*, 1997; 6(1): 72-75). Tocotrienols have been known to be beneficial for maintaining a healthy cardiovascular system.

Carotenoids are oil soluble yellow to orange red pigments found in many plants and animals. There are generally two classes of carotenoids, carotenes and xanthophylls. Carotenes are hydrocarbon carotenoids while xanthophylls are oxygenated carotenoids. Carotenoids are a group of highly unsaturated compounds and are easily decomposed by heat, light and oxygen. The more widely known carotenes are alpha, beta and gamma carotenes and lycopene. Beta-carotene and alpha-carotene are precursors of vitamin A and have been shown to inhibit tumor growth (Giovannucci E, et al., *Am. J. Clin Nutr.*, Vol. 7294; 990-997, 2000; Murakoshi, M, et al. *Cancer Research*, 52; 6583-6587, 1992.). Carotenoids are present in most fruits, vegetables and numerous vegetable oils. Of the vegetable oils that are widely consumed, palm oil contains the highest known concentration of naturally derived carotenoids.

Phytosterols (including plant sterols and stanols) are natural components of edible vegetable oils such as palm oil, soy bean oil, sunflower seed oil and, as such are natural constituents of the human diet. These plant lipid-like compounds are present at low levels in grains, fruits and vegetables. There are approximately 250 different sterols and related compounds in plant and marine materials with the most common ones beta-sitosterol, stigmasterol, and campesterol.

A large body of scientific research dating back to the 1950s has documented the ability of phytosterols to block the absorption of cholesterol and reduce blood cholesterol levels. Because cholesterol and phytosterol molecules are similar, the human body can't tell the difference. Phytosterols compete with cholesterol for absorption in the small intestine. However, phytosterols themselves are not absorbed by the human body.

Historically, extraction and purification of tocotrienols/tocopherols (hereinafter referred to as tocols), carotenoids and sterols has been incomplete, low yield (not economically feasible) and involved intensive capital investment. For example, carotenoids have been extracted from crude palm oil but the tocols and sterols are typically lost during the extraction process. Like wise, carotenoids are lost during the extraction of tocols or sterols from oils. Known processes used are solvent extraction, solvent fractionation, ion exchange resin treatment and chromatography method. Most of these commercial production methods are not successful or economically attractive with low yield and substantial degradation of compounds with alteration of the natural ratio of the various isomers of tocotrienols and carotenoids after separation and purification. In addition, the chromatographic method employs the use of organic solvents, which are known to be carcinogenic.

This present invention provides a novel and efficient method for the extraction and purification of tocotrienols/tocopherols, carotenoids and sterols from oils that is simple, cost efficient with high yield as well as retaining the natural composition and ratio of the natural tocotrienols/tocopherols, carotenoids and sterols as found in the starting oils. The tocols and carotenoids concentrate are produced without the use of harmful organic solvents such as hexane, heptane or etc.

SUMMARY OF THE INVENTION

Accordingly, it is the object of the present invention to provide an integrated process for the extraction and purification of tocols, carotenoids and sterols present in vegetable oils.

This and other objectives of the present invention is accomplished by,

An integrated process for extracting and purifying tocotrienols/tocopherols, carotenoids and sterols and production of fatty acid esters from oils, comprising the steps of:

a. Trans-esterification of oil containing tocotrienols/tocopherols, carotenes, sterols, fatty acids, mono-, di- and triglycerides, for a period of time at specific temperature in the presence of a monohydric alcohol, and base or acid to form an ester-rich layer and a glycerol-rich layer;

b. Separating the ester-rich layer from the glycerol-rich layer as obtained in (a) by gravitational settling, decantation or separation by centrifugal forces;

c. Washing and drying the ester-rich layer obtained in (b) under conditions sufficient to remove all impurities and base or acid without destroying the tocotrienols, tocopherols and carotenoids in the ester-rich layer;

d. Step-wise molecular distillation or any other distillation of the resultant dried ester-rich layer as obtained in (c) to yield a concentrated mixture of tocotrienols/tocopherols, carotenoids and sterols at specific temperature and pressure;

e. Further trans-esterification of the mixture obtained in (d) containing concentrated tocotrienols/tocopherols, carotenes, sterols, fatty acids, mono-, di- and triglycerides, for a period of time at specific temperature in the presence of a monohydric alcohol, and base or acid to convert glycerides in the oil to form an ester-super-rich layer and a glycetol-rich layer; and f. Repeating the above trans-esterification reactions and stepwise molecular distillations to achieve the desired concentration of tocotrienols/tocopherols, carotenoids and sterols.

Stage One: First Trans-Esterification

Stage One involves the trans-esterification of the oil with a lower alkyl alcohol in the presence of a base under conditions sufficient to convert glycerides in the oil to fatty acid alkyl esters and glycerol and to form an ester-rich layer and a glycerol-rich layer.

The glycerol-rich layer is then separated from the ester-rich layer via the gravitational settling or the use of a separator or centrifuge. The remaining ester-rich layer is then subjected to conventional direct hot water washing or counter current hot-water washing process and subsequently drying of the washed ester-rich layer via vacuum drying process prior to molecular distillation. At the end of the multi-stage molecular distillation, there are two steam of products—distilled fatty acid alkyl ester (FAAE) and concentrated blend of carotenoids, tocols and sterols (Concentrate-1). This Concentrate-1 is then subjected to further processing (ie: Stage-Two: Second Trans-Esterification).

The FAAE can be sold as it is or further fractionated to various alkyl ester cut (various combination of carbon-chain length of alkyl esters) and sold as an oleochemical product.

Stage Two: Second Trans-Esterification

The Concentrate-1 from Stage One—First Esterification Reaction is further subjected to trans-esterification reaction which involves a lower alkyl alcohol in the presence of a base under conditions sufficient to convert as much of the remaining glycerides in the Concentrate-1 to fatty acid alkyl esters and glycerol to form an ester-super-rich layer and a glycerol-rich layer. The resulting mixture can be either i) washed with hot water to take out impurities such as glycerol or ii) subjected to a separator or centrifuge to take out the glycerol and followed by a direct how water washing or counter-current hot water washing process.

The remaining ester-super-rich layer is then subjected to conventional direct hot water washing or counter current hot-water washing process and subsequently drying of the washed ester-super-rich layer via vacuum drying process prior to molecular distillation.

At the end of the multi-stage molecular distillation, there are two steam of products—distilled fatty acid alkyl ester (FAAE) and concentrated blend of carotenoids, tocols and sterols (Concentrate-2). This Concentrate-2 is then subjected to further multi-stage molecular distillation to separate out the carotenoids concentrate from tocol/sterol mixture.

The carotenoids concentrate obtained from Concentrate-2 is further subjected to alcoholic washing by contacting it with a lower alkyl alcohol or combination of lower alkyl alcohols under conditions sufficient to remove any impurities in the carotenoids concentrate. The lower alkyl alcohol is decanted via settling process or centrifugation forces. This alcoholic washing process can be repeated several times to achieve the desired concentration of carotenoids. After the alcoholic washing, any remaining methanol or combination of lower alkyl alcohol is evaporated out via vacuum evaporation or distillation with a wiped film evaporator or short path distillation.

On the other hand, the tocols/sterol mixture obtained from Concentrate-2 is further subjected to crystallization in the presence of a lower alkyl alcohol or combination of low alkyl alcohols at low temperature. The reduction of temperature during the crystallization process can be carried out on a step-wise basis to ensure optimum crystallization of sterols and can also be repeated several times to achieve the desired concentration of tocols in the alkyl alcohol (tocol-rich alkyl alcohol) and crystallized sterols. A slow and gentle stirring can be applied during crystallization to induce the sterols to precipitate out.

The crystallized sterols is separated out from the tocol-rich lower alkyl alcohol via a filter press or other means of solid-liquid separation such as separator/centrifugation, vacuum filtration, etc. The alkyl alcohol in the tocol-rich alkyl alcohol is removed via vacuum evaporation or distillation with a wiped film evaporator or short path distillation. The resulting tocols concentrate may also contain other compounds such as squalene, sterols, carotenoids and CoQ10.

The crystallized and filtered sterols is then dried using the conventional air drying method or oven method or fluid bed-dryer method. The dried sterols are then contacted with solvents selected from the group consisting of but not limited to, hexane, heptane, isooctane, acetone or ethyl acetate. The selected solvent will dissolve the remaining glycerides (mono-, di- and triglyceride) with sterols remaining as solid in the solvent. The crystallized sterols is separated out from the solvent via a filter press or other means of solid-liquid separation such as separator/centrifugation, vacuum filtration, etc. The solvent in the sterols is evaporated out via vacuum evaporation or distillation with a wiped film evaporator or short path distillation.

This invention has many advantages. In general, it provides an economical and improved process for extraction and purification of tocols, carotenoids and sterols from oil such as crude palm oil or crude palm olein or red palm oil/olein and other types of oils. Further separation of individual components at high concentration can be economically achieved.

DETAILED DESCRIPTION OF THE INVENTION

This invention provides an integrated process for the extraction and purification of tocotrienols/tocopherols, carotenoids and sterols from vegetable or edible oils containing tocotrienols/tocopherols, carotenoids and sterols. Suitable oils include but not limited to, crude palm oil, crude palm olein, red palm oil/olein, palm stearin, neutralized red palm oil, neutralized red palm olein, sunflower oil, coconut oil, wheat germ, carrot oil, soybean, rapeseed, olive and derivative of such oils.

Stage One: First Trans-Esterification

Stage One involves the trans-esterification of the oil with an esterification solution comprising of a lower alkyl alcohol in the presence of a base or acid under conditions sufficient to convert glycerides in the oil to fatty acid alkyl esters and glycerol and to form an ester-rich layer and a glycerol-rich layer. The alkyl esters produced in this trans-esterification process are preferably the methyl, ethyl, and isopropyl or butyl esters of the fatty acids. In this invention, lower alkyl alcohols are alcohols with saturated carbon chains between one and four carbons. Such examples of lower alkyl alcohol are but not limited to, methanol or ethanol or isopropanol or butanol. In this invention, the base comprises of but not limited to, sodium methoxide or sodium hydroxide with methanol or potassium hydroxide with methanol while the acid catalysts comprise of but not limited to hydrochloric acid or phosphoric acid or citric Acid.

Esterification solution such as sodium methoxide or sodium hydroxide with methanol or potassium hydroxide with methanol is the preferred catalysts for conversion of glycerides in the oil into alkyl esters at temperature of 5° C. to 90° C. for a period of 0.5 hour to 16 hours with agitation of between 10-500 rpm. The ratio of oil to the esterification solution is in the range between 0.5-10 part of oil to 1 part esterification solution. The ratio of base to lower alkyl alcohol in the esterification solution is in the range between 0.005 to 5 part of base to 1 part of lower alkyl alcohol.

The glycerol-rich layer is then separated from the ester-rich layer via the gravitational settling or the use of a separator/centrifuge. The glycerol-rich layer with 10-60% glycerol level (also known as crude glycerine) is then refined to higher purity glycerine with typical glycerol concentration of between 80-99%. The remaining ester-rich layer which contains the tocols, carotenoids and sterols is then subjected to conventional hot water washing or counter current hot-water washing process and subsequently drying of the washed ester-rich layer via vacuum drying process prior to molecular distillation. In one preferred embodiment, the remaining ester-rich layer undergoes counter-current or conventional means of direct washing out of the remaining glycerol content and all impurities soluble in the aqueous phase. The hot water used is at the range of 5° C. to 90° C. The washing process is under conditions sufficient to remove all impurities and base or acid remnants from the ester-rich layer and preserving the quality and integrity of tocotrienols/tocopherols, carotenoids and sterols in the ester-rich layer itself. In the preferred embodiment, hot water ranging from one to ten volumes per volume of ester-rich layer is used to substantially remove any base or acid remaining in the ester-rich layer. This hot water wash process is repeated as many times as required to achieve a pH of between 6-8 in the ester-rich layer. A lower water layer containing base or acid from the ester-rich layer is thereby formed.

This lower water layer can be separated out from the ester-rich layer via settling process and decanted out or via a separator/centrifuge. The washed ester-rich layer is then subjected to a drying process to remove as much water/moisture as possible which involves a vacuum drying process at temperature ranging from 50-200° C. and vacuum of 5-100 mbar for 30 minutes to 10 hours. Moisture content in the dried ester-rich layer ranges from 0.001% to 0.20%.

The dried ester-rich layer is then subjected to a multi-stage molecular distillation. The multi-stage molecular distillation process involves vacuum distillation operating at 0.00001 mbar to 1.0 mbar and at temperature ranging from 50° C. to 300° C. At the end of the multi-stage molecular distillation, there are two steam of products—distilled fatty acid alkyl ester (FAAE) and concentrated blend of carotenoids, tocols and sterols (Concentrate-1). The concentration of each of these individual components in Concentrate-1 are typically 0.1%-10% tocols, 0.1%-10% carotenoids and 0.1%-10% sterols. This Concentrate-1 is then subjected to further processing (ie: Stage-Two: Second Trans-Esterification).

The FAAE can be sold at it is or further fractionated to various alkyl ester cut (various combination of carbon-chain length of alkyl esters) and sold as an oleochemical product.

Stage Two: Second Trans-Esterification

The Concentrate-1 from Stage One: First Trans-Esterification reaction is subjected to trans-esterification reaction which involves a lower alkyl alcohol in the presence of a base under conditions (esterification solution) sufficient to convert as much of the remaining glycerides in the Concentrate-1 to fatty acid alkyl esters and glycerol to form an ester-super-rich layer and a glycerol-rich layer. Sodium methoxide or sodium hydroxide with methanol or potassium hydroxide with methanol is the preferred catalysts for conversion of glycerides in the Concentrate-1 into alkyl esters at temperature of 5° C. to 90° C. for a period of 0.5 hour to 16 hours with agitation between 10-500 rpm. The ratio of Concentrate-1 to the esterification solution is in the range between 0.5-10 part of oil to 1 part esterification solution. The ratio of base or acid to lower alkyl alcohol in the esterification solution is in the range between 0.005 to 5 part of base or acid to 1 part of lower alkyl alcohol.

The resulting mixture can be either i) washed with hot water to take out impurities such as glycerol or ii) subjected to a separator or centrifuge to take out the glycerol and followed by a direct how water washing or counter-current hot water washing process of the ester-super-rich layer.

The remaining ester-super-rich layer which contains tocols, carotenoids and sterols is then subjected to conventional hot water washing or counter current hot-water washing process and subsequently drying of the washed ester-super-rich layer via vacuum drying process prior to molecular distillation.

In one preferred embodiment, the remaining ester-super-rich layer undergoes counter-current or conventional means of direct washing out of the remaining glycerol content and all impurities soluble in the aqueous phase. The hot water used is at the range of 5° C. to 90° C. The washing process is under conditions sufficient to remove all impurities and base or acid remnants from the ester-super-rich layer and preserving the quality and integrity of tocotrienols/tocopherols, carotenoids and sterols in the ester-super-rich layer itself. In the preferred embodiment, hot water ranging from one to ten volumes per volume of ester-super-rich layer is used to substantially remove any base or acid remaining in the ester-super-rich layer. This hot water wash process is repeated as many times as required to achieve a pH of between 6-8 in the ester-super-rich layer. A lower water layer containing base or acid from the ester-super-rich layer is thereby formed.

This lower water layer can be separated out from the ester-super-rich layer via settling process and decanted out or via a separator/centrifuge. The washed ester-super-rich layer is then subjected to a drying process to remove as much water/moisture as possible which involves a vacuum drying process at temperature ranging from 50-200° C. and vacuum of 5-100 mbar for 30 minutes to 10 hours. Moisture content in the dried ester-super-rich layer ranges from 0.001% to 0.20%.

The dried ester-super-rich layer is then subjected to a multi-stage molecular distillation. The multi-stage molecular distillation process involves vacuum distillation operating at 0.00001 mbar to 1.0 mbar and at temperature ranging from 50° C. to 300° C. At the end of the multi-stage molecular distillation, there are two steam of products—distilled fatty acid alkyl ester (FAAE) and concentrated blend of carotenoids, tocols and sterols (Concentrate-2). The concentration of each of these individual components in Concentrate-2 are typically 5%-50% tocols, 5%-30% carotenoids and 5%-50% sterols.

This Concentrate-2 is again subjected to further multi-stage molecular distillation to separate out the carotenoids concentrate from tocol/sterol mixture. The multi-stage molecular distillation is carried out at temperature between 50° C. to 300° C. and vacuum of between 0.00001 to 1.0 mbar. The tocols/sterol mixture is distilled out as the distillate whereas the carotenoids concentrate remains as the residue. The typical concentration of total tocos and sterols in the tocols/sterols mixture is 5%-30% and 5-50% respectively. The total carotenoids concentration in the residue is between 5%-30%

The carotenoids concentrate obtained from multi-stage molecular distillation of Concentrate-2 is further subjected to alcoholic washing by contacting it with a lower alkyl alcohol under conditions sufficient to remove any impurities. Suitable lower alkyl alcohols for alcoholic washing include but not limited to, methanol or ethanol or propanol or butanol or isopropyl alcohol or combination of these alkyl alcohols. In one preferred embodiment, the lower alkyl alcohol comprises of methanol or a mixture of one or more types of lower alkyl alcohols is incorporated. The ratio of lower alkyl alcohol for the alcoholic washing is in the range of between one volume to twenty volumes per volume of carotenoids concentrate. In one embodiment, about one to five volumes of methanol per volume of carotenoid rich layer are incorporated. The selected alkyl alcohol and carotenoids concentrate are agitated for a period of time with half an hour to 30 hours at a temperature in the range of between 5° C. to 90° C. The top layer of alkyl alcohol is then decanted out. This alcoholic washing process can be repeated several times to achieve the desired concentration of carotenoids. After the alcoholic washing, any remaining the methanol or combination of lower alkyl alcohol is evaporated out via vacuum evaporation or distillation with a wiped film evaporator or short path distillation. The resulting carotenoids concentrate has a carotene concentration of between 20-50%.

The tocols/sterol mixture obtained from multi-stage molecular distillation of Concentrate-2 is further subjected to crystallization in the presence of a lower alkyl alcohol or combination of low alkyl alcohol at low temperature. The low alkyl alcohol can be selected from but not limited to, methanol or ethanol or propanol or butanol or isopropyl alcohol or combination of these alkyl alcohols. In one preferred embodiment, the lower alkyl alcohol comprises of methanol mixture of one or more types of lower alkyl alcohols are utilized. The ratio of lower alkyl alcohol is in the range of between one volume to twenty volumes per volume of tocol/sterols mixture. In one embodiment, about one to five volumes of methanol per volume of tocols/sterol mixture are used. The selected alkyl alcohol and tocols/sterols mixture are agitated for a period of time and the crystallization temperature ranges from −60° C. to 0° C. for a period of 3 hours to 10 days.

The reduction of temperature during the crystallization can be carried out on a step-wise basis to ensure optimum crystallization of sterols and can be repeated several times to achieve the desired concentration of tocols in the alkyl alcohol (tocol-rich alkyl alcohol) and crystallized sterols.

The crystallized sterols is separated out from the tocol-rich lower alkyl alcohol via a filter press or other means of solid-liquid separation such as separator/centrifugation, vacuum filtration, etc. The alkyl alcohol in the tocol-rich alkyl alcohol is evaporated out via vacuum evaporation or distillation with a wiped film evaporator or short path distillation. The resulting tocols concentrate has a tocotrienols/tocopherol of between 20-90%. The tocols concentrate may also contain other compounds such as squalene, sterols, carotenoids and CoQ10 with typical concentration ranges between 0.5-20%, 0.5-20%, 0.05-10% and 0.001-2% respectively.

The filtered or crystallized sterols have a total sterols concentration of between 10-60%. It is then dried using the conventional air drying method or oven method or fluid bed-dryer method. The dried sterols are then contacted with solvents selected from the group consisting of but not limited to, hexane or heptane or isooctane or acetone or ethyl acetate. The selected solvent will dissolve the remaining glycerides (mono-, di- and triglyceride) with sterols remaining as solid in the solvent. The crystallized sterols is separated out from the solvent via a filter press or other means of solid-liquid separation such as separator/centrifugation, vacuum filtration, etc. This process of washing with solvent such as hexane can be repeatedly carried out to achieve the desired phytosterol concentration and color. In one preferred embodiment, the crystallized sterols is washed with hexane and filtered between 5-30 times and the ratio of the crystallized sterols to hexane in this washing process ranges from 1:1 to 10:1. The resulting filtered sterols would have a concentration ranging from 30-90% of total sterols.

Once the desired concentration is achieved, the filtered sterol is dissolved in solvents selected from the group consisting of but not limited to, hexane or heptane or isooctane or acetone or ethyl acetate hexane. The ratio of filtered sterols to solvent ranges from 1:1 to 10:1. The mixture is then slightly heated up to temperature between 10-80° C. to dissolve the sterols in the solvent used. Once dissolved, the mixture is chilled down to temperature between −30° C. to 10° C. in a process called crystallization. The crystallization time is between 12-72 hours. At the end of the crystallization process, the crystallized sterols are filtered out with a filter press or other solid-liquid methods of separation. The resultant sterol is dried with a spray-drying machine or other drying methods to a white powder with a phytosterol content between 70-99%. In one preferred embodiment, the 200 kg of filtered sterols at 40% concentration of sterols is dissolved in 1400 L of hexane and heated up to 50° C. This mixture is then chilled to −20° C. for 36 hours. At the end of the crystallization process, the crystallized sterols are filtered out again using a filter press. The resultant sterol is spray-dried to a white powder with 90% phytosterol content.

The final tocols concentrate with tocotrienols/tocopherols concentration of between 20-90% has small level of carotenoids (0.001%-2%). For the topical application especially topical creams, the carotenoids are undesirable component as it give rise to a yellow colour in the topical cream. This carotenoids in the tocols concentrate can be removed via a simple decolourization and/or deodourization process. The tocols concentrate is contacted with a solvent selected from the group consisting of but not limited to, hexane or heptane or isooctane or acetone or ethyl acetate or a mixture of these solvents. The mixture thereafter is subjected to treatment with absorbent such as but not limited to, bleaching earth or activated carbon, at a ratio of one part to ten parts or absorbent to per part of the tocols concentrate mixture for a period of time at specific temperature. In one preferred embodiment, the treatment ranges from 1 hour to 24 hours at temperature of 10° C. to 90° C. The mixture is agitated at between 10 rpm to 1000 rpm. Upon completion of the said treatment, the decolourized filtrate is separated from the absorbent, bleaching earth or activated carbon with a simple filtration using filter press or vacuum filtration, centrifugation or simple settling and decantation. The clear lighter coloured filtrate thereafter undergoes an evaporation process via a vacuum evaporator, wiped-film evaporator, or short path distillation at temperature range of 10 C. to 90 C. and vacuum of 1 mbar to 0.0001 mbar to remove all the solvents and leaving behind a concentrated decolorized tocols concentrate suitable for use in the cosmetics industry. The colour reduction of the said process ranges from 20 R to 80 R (measured with a 5½ inch cell of a Lovibond Tintometer or APHA colour measuring equipment) in the starting tocols concentrate to between 1 R to 20 R in the final decolourized tocols concentrate.

While particular embodiments of the subject invention have been described, it will be obvious to those skilled in the art that various changes and modifications to the subject invention can be made without departing from the spirit and scope of the invention. It is intended to cover, in the appended claims, all-such modifications that are within the scope of this invention.

The invention claimed is:

1. An integrated process for extracting and purifying tocotrienols/tocopherols, carotenoids and sterols and production of fatty acid esters from oils, comprising the steps of:
   a. tran-esterification of oil containing tocotrienols/tocopherols, carotenes, sterols, fatty acids, mono-, di- and triglycerides, for a period of time at specific temperature in the presence of a monohydric alcohol, and base or acid to form an ester-rich layer and a glycerol-rich layer;
   b. separating the ester-rich layer from the glycerol-rich layer as obtained in (a) by gravitational settling, decantation or separation by centrifugal forces;
   c. washing and drying the ester-rich layer obtained in (b) under conditions sufficient to remove all impurities and base or acid without destroying the tocotrienols, tocopherols and carotenoids in the ester-rich layer;
   d. step-wise molecular distillation or any other distillation of the resultant dried ester-rich layer as obtained in (c) to yield a concentrated mixture of tocotrienols/tocopherols, carotenoids and sterols at specific temperature and pressure;
   e. further trans-esterification of the mixture obtained in (d) containing concentrated tocotrienols/tocopherols, carotenes, sterols, and fatty acids, mono-, di- tri glycerides, for a period of time at specific temperature in the presence of a monohydric alcohol, and base or acid to convert glycerides in the oil to form an ester-super-rich layer and a glycerol-rich layer; and
   f. repeating the above trans-esterification reactions and step-wise molecular distillations to achieve the desired concentration of tocotrienols/tocopherols, carotenoids, and sterols.

2. The process according to claim 1, wherein the concentrated carotenoids are treated with a lower alkyl alcohol under conditions sufficient to form carotenoids miscelles without destroying the carotenoids, thereby forming a carotenoid-rich layer.

3. The carotenoid-rich layer according to claim 2, wherein the said carotenoid-rich layer is subjected to an evaporation or distillation process to distill out the lower alkyl alcohol to form a concentrated carotenoid extract.

4. The process according to claim 1, wherein the concentrated tocotrienols/tocopherols/sterols mixture is treated with a low monohydric alcohol for a period of time at specific temperature to crystallize out the sterols and mono-, di-, and tri-glycerides from the mixture.

5. The concentrated tocotrienols/tocopherols/sterols mixture according to claim 4, wherein the said mixture is subjected to a solid-liquid filtration to yield a rich tocotrienols/tocopherols filtrate and sterols cake.

6. The tocotrienols/tocopherols filtrate according to claim 5, wherein the said filtrate is subjected to an evaporation or distillation process to distill out the lower alkyl alcohol to form a concentrated tocotrienols/tocopherols extract.

7. The sterols cake according to claim 5, wherein the sterols cake is treated with appropriate solvents for a period of time at specific temperature to concentrate the sterols.

8. The concentrated tocotrienols/tocopherols extract obtained from the crystallization process as in claim 4, wherein the said tocotrienols/tocopherols concentrate is treated with appropriate solvents and absorbents, bleaching earth or activated carbon for a period of time at specific temperature to reduce the color, and to obtain a lighter colored tocotrienols/tocopherols concentrate.

9. The process according to claim 1, wherein the oil used in the transesterification is selected from the group consisting of crude palm oil, crude palm olein, red palm oil, red palm olein, vegetable oil and any other suitable edible oil.

10. The process according to claim 1, wherein glycerides in the oil are converted to fatty acid alkyl esters and glycerol, and to form an ester-rich layer and a glycerol-rich layer, by contacting the oil with an esterification solution comprising lower alkyl alcohol and a base or acid.

11. The process according to claim 1, wherein the ratio of oil to the esterification solution is in the range between 0.5-10 part of oil to 1 part esterification solution.

12. The process according to claim 1, wherein the base used in the esterification solution is selected from a group consisting of sodium methoxide, potassium methoxide, sodium hydroxide, potassium hydroxide, and any other suitable base.

13. The process according to claim 1, wherein the ratio of base to lower alkyl alcohol in the esterification solution is in the range between 0.005 to 5 part of base to 1 part of lower alkyl alcohol.

14. The process according to claim 1, wherein the acid used is selected from a group consisting of hydrochloric acid, phosphoric acid, citric acid and any other suitable acid.

15. The process according to claim 1, wherein the ratio of acid to lower alkyl alcohol in the esterification solution is in the range between 0.005 to 5 part of acid to 1 part of lower alkyl alcohol.

16. The process according to claim 1, wherein the lower alkyl alcohol used is selected from the group consisting of methanol, ethanol, butanol, propanol and any other suitable lower alkyl alcohol.

17. The process according to claim 1, wherein the trans-esterification is carried out at a temperature ranging from 5° C. to 90° C. with a time period ranging from 0.50 hour to 16 hours.

18. The process according to claim 1, wherein the trans-esterification mixture is agitated at a speed of between 10 rpm to 500 rpm.

19. The process according to claim 1, wherein the alkyl esters produced comprise methyl, ethyl, and isopropyl or butyl esters of the fatty acids, depending on the type of lower alkyl alcohol used.

20. The process according to claim 1, wherein the ester-rich layer or ester-super-rich layer is separated from the glycerol-rich layer by conventional gravitational settling or centrifugal forces.

21. The process according to claim 1, wherein the ester-rich layer or ester-super-rich layer is washed with either hot or cold water via direct contact with the hot water or through a counter-current hot water column at a temperature ranging between 30 to 90° C.

22. The process according to claim 1, wherein the ester-rich layer or ester-super-rich layer is washed with hot water until a pH of 6 to 8 is reached.

23. The process according to claim 1, wherein the washed ester-rich layer or ester-super-rich layer is subjected to vacuum evaporation or wiped film evaporator or short path distillation to achieve a moisture content of between 0.001% to 0.20%.

24. The process according to claim 1, wherein the dried ester-rich layer or ester-super-rich layer is subjected to a multi-stage molecular distillation at a temperature ranging from of 50° C. to 300° C. and at a vacuum of 0.00001 to 1.0 mbar.

25. The process according to claim 1, wherein the mixture obtained in 1(d) comprises a concentrated mixture of tocotrienols/tocopherols, carotenoids and sterols at a concentration of between 0.1-10%, 0.1-10% and 0.1-10% respectively.

26. The process according to claim 1, wherein the multi-stage molecular distillation of the dried ester-super-rich layer will produce tocotrienols/tocopherols/sterols extract as the distillate and carotenoids extract as the residue.

27. The process according to claim 1, wherein the content of tocotrienols/tocopherols/sterols in the distillate is 5% to 30% total tocotrienols/tocopherols and 5%-50% total sterols and carotenoids content in the residue is between 5%-30%.

28. The process according to claim 2, wherein the lower alkyl alcohol used in alcoholic washing is selected from the group consisting of methanol, ethanol, propanol, butanol, isopropyl alcohol and any combination of these alkyl alcohols.

29. The process according to claim 2, wherein the washing and agitation time ranges from half an hour to 30 hours and the temperature ranges from between 5° C. to 90° C.

30. The process according to claim 2, wherein the concentrated carotenoids extract has a concentration of between 20%-50% total carotenoids.

31. The process according to claim 2, wherein the concentrated carotenoids extract consists of alpha-carotene and beta-carotene as the major carotenoids and other carotenoids, at lower concentration.

32. The process according to claim 4, wherein the lower alkyl alcohol used in the crystallization of tocotrienols/tocopherols/sterols mixture is selected from the group consisting of methanol, ethanol, propanol, butanol and any combination of these alkyl alcohols.

33. The process according to claim 4, wherein the crystallization temperature ranges from 60° C. to 0° C. for a period ranging from 3 hours to 10 days.

34. The process according to claims 4, wherein the evaporation temperature ranges from 10° C. to 90° C.

35. The process according to claim 4, wherein the resulting tocols concentrate has a total concentration of tocotrienols and tocopherols ranging from between 20% to 90%.

36. The process according to claim 4, wherein the resulting tocols concentrate comprises alpha-tocopherol, beta-tocopherol, gamma-tocopherol, delta-tocopherol and alpha-tocotrienol, beta-tocotrienol, gamma-tocotrienol and delta-tocotrienol.

37. The process according to claim 4, wherein the resulting tocols concentrate may also contain squalene, sterols, carotenoids and CoQ10 with typical concentration ranging between 0.5%-20%, 0.5%-20%, 0.05%-10% and 0.001%-2% respectively.

38. The process according to claim 5, wherein the solvent used in the purification of sterols is selected from the group consisting of hexane, heptane, iso-octane, acetone, ethyl acetate and any combination of these solvents, in the ratio ranging from between 1:1-10:1.

39. The process according to claim 5, wherein the crystallization of sterols is carried out at a temperature ranging from 30° C. to 10° C. for 12 to 72 hours and the resulting filtered and dried sterols have a total phytosterols content ranging from 70% to 90%.

40. The process according to claim 5, wherein the temperature range of the purification of sterols is between 10° C. to 80° C. and the time period ranges from 1 to 10 hours.

41. The process according to claim 8, wherein the temperature range of the decolourization process is between 10° C. to 90° C. and the time period ranges from 1 to 24 hours per batch.

42. The process according to claim 8, wherein the mixture is agitated in the range from 10 rpm to 1000 rpm.

43. The process according to claim 8, wherein the mixture after reaction is filtered with filter press or vacuum filtration or centrifugation or simple settling and the resulting filtrate is evaporated at temperature ranging from 10° C. to 90° C. and at a vacuum of between 1 mbar to 0.0001 mbar.

44. The process according to claim 8, wherein the final decolourized tocols concentrate has a colour range of between 1 R to 20 R when measured with a 5½ inch cell of the Lovibond Tintometer.

45. Tocotrienols, tocopherols, carotenoids and sterols produced from oils according to the process as in claim 1.

46. The process according to claim 12, wherein the ratio of base to lower alkyl alcohol in the esterification solution is in the range between 0.005 to 5 part of base to 1 part of lower alkyl alcohol.

47. The process according to claim 14, wherein the ratio of acid to lower alkyl alcohol in the esterification solution is in the range between 0.005 to 5 part of acid to 1 part of lower alkyl alcohol.

48. The process according to claim 26, wherein the content of tocotrienols/tocopherols/sterols in the distillate is 5% to 30% total tocotrienols/tocopherols and 5%-50% total sterols and carotenoids content in the residue is between 5%-30%.

49. The process according to claim 3, wherein the lower alkyl alcohol used in alcoholic washing is selected from the group consisting of methanol, ethanol, propanol, butanol, isopropyl alcohol and any combination of these alkyl alcohols.

50. The process according to claim 3, wherein the washing and agitation time ranges from half an hour to 30 hours and the temperature ranges from between 5° C. to 90° C.

51. The process according to claim 3, wherein the concentrated carotenoids extract has a concentration of between 20%-50% total carotenoids.

52. The process according to claim 3, wherein the concentrated carotenoids extract consists of alpha-carotene and beta-carotene as the major carotenoids and other carotenoids such as gamma-carotene, lycopene, phytoene and phytofluene at lower concentration.

53. The process according to claim 5, wherein the lower alkyl alcohol used in the crystallization of tocotrienols/tocopherols/sterols mixture is selected from the group consisting of methanol, ethanol, propanol, butanol and any combination of these alkyl alcohols.

54. The process according to claim 6, wherein the lower alkyl alcohol used in the crystallization of tocotrienols/tocopherols/sterols mixture is selected from the group consisting of methanol, ethanol, propanol, butanol and any combination of these alkyl alcohols.

55. The process according to claim 5, wherein the crystallization temperature ranges from 60° C. to 0° C. for a time period ranging from 3 hours to 10 days.

56. The process according to claim 6, wherein the crystallization temperature ranges from 60° C. to 0° C. for a time period ranging from 3 hours to 10 days.

57. The process according to claim 5, wherein the evaporation temperature ranges from 10° C. to 90° C.

58. The process according to claim 6, wherein the evaporation temperature ranges from 10° C. to 90° C.

59. The process according to claim 5, wherein the resulting tocols concentrate has a total concentration of tocotrienols and tocopherols ranging from between 20% to 90%.

60. The process according to claim 6, wherein the resulting tocols concentrate has a total concentration of tocotrienols and tocopherols ranging from between 20% to 90%.

61. The process according to claim 5, wherein the resulting tocols concentrate comprises alpha-tocopherol, beta-tocopherol, gamma-tocopherol, delta-tocopherol and alpha-tocotrienol, beta-tocotrienol, gamma-tocotrienol and delta-tocotrienol.

62. The process according to claim 6, wherein the resulting tocols concentrate comprise alpha-tocopherol, beta-tocopherol, gamma-tocopherol, delta-tocopherol and alpha-tocotrienol, beta-tocotrienol, gamma-tocotrienol and delta-tocotrienol.

63. The process according to claim 5, wherein the resulting tocols concentrate may also contain squalene, sterols, carotenoids and CoQ10 with typical concentration ranging between 0.5%-20%, 0.5%-20%, 0.05%-10% and 0.001%-2% respectively.

64. The process according to claim 6, wherein the resulting tocols concentrate may also contain squalene, sterols, carotenoids and CoQ10 with typical concentration ranging between 0.5%-20%, 0.5%-20%, 0.05%-10% and 0.001%-2% respectively.

65. The process according to claim 7, wherein the solvent used in the purification of sterols is selected from the group consisting of hexane, heptane, iso-octane, acetone, ethyl acetate and any combination of these solvents, in the ratio ranging from between 1:1-10:1.

66. The process according to claim 7, wherein the crystallization of sterols is carried out at a temperature ranging from 30° C. to 10° C. for 12 to 72 hours and the resulting filtered and dried sterols have a total phytosterols content ranging from 70% to 90%.

67. The process according to claim 7, wherein the temperature range of the purification of sterols is between 10° C. to 80° C. and the period ranging from 1 to 10 hours.

* * * * *